United States Patent
Caccamo

(10) Patent No.: US 10,555,383 B1
(45) Date of Patent: Feb. 4, 2020

(54) SMOKE DETECTING MICROWAVE ASSEMBLY

(71) Applicant: Sebastian Caccamo, Rochester, NY (US)

(72) Inventor: Sebastian Caccamo, Rochester, NY (US)

( * ) Notice: Subject to any disclaimer, the term of this patent is extended or adjusted under 35 U.S.C. 154(b) by 0 days.

(21) Appl. No.: 16/050,536

(22) Filed: Jul. 31, 2018

(51) Int. Cl.
*H05B 6/64* (2006.01)
*G01N 33/00* (2006.01)
*H05B 6/66* (2006.01)
*G08B 17/117* (2006.01)
*H05B 6/68* (2006.01)

(52) U.S. Cl.
CPC ......... *H05B 6/6461* (2013.01); *G01N 33/004* (2013.01); *G01N 33/0063* (2013.01); *G08B 17/117* (2013.01); *H05B 6/666* (2013.01); *H05B 6/687* (2013.01)

(58) Field of Classification Search
CPC ...... H05B 6/6461; H05B 6/666; H05B 6/687; F23N 5/242; F24C 14/02; F24C 7/087; G08B 17/10; G08B 17/117; G08B 21/14; G01N 33/004; G01N 33/0063
See application file for complete search history.

(56) References Cited

U.S. PATENT DOCUMENTS

| | | | |
|---|---|---|---|
| 4,319,110 A | 3/1982 | Tanabe | |
| 4,496,817 A | 1/1985 | Smith | |
| 6,046,441 A * | 4/2000 | Daffron | F24C 7/08 219/413 |
| 8,138,933 B2 | 3/2012 | Crucs | |
| 9,153,113 B1 | 10/2015 | Jones | |
| D789,511 S | 3/2017 | Chung | |
| 10,013,872 B1* | 7/2018 | Seigler | G08B 29/043 |
| 2001/0052852 A1* | 12/2001 | Kouznetsov | F24C 7/087 340/630 |
| 2004/0144768 A1* | 7/2004 | Odorcic | F24C 7/087 219/391 |
| 2005/0265423 A1* | 12/2005 | Mahowald | H05B 6/687 374/121 |
| 2006/0164253 A1* | 7/2006 | Harvey | G08B 17/10 340/628 |
| 2008/0018484 A1 | 1/2008 | Sager | |
| 2010/0073174 A1 | 3/2010 | Dufour | |
| 2010/0109887 A1* | 5/2010 | Crucs | F23N 5/242 340/628 |
| 2010/0201531 A1* | 8/2010 | Pakravan | G08B 21/14 340/632 |

(Continued)

FOREIGN PATENT DOCUMENTS

WO WO2010053746 5/2010

*Primary Examiner* — Orlando Bousono

(57) ABSTRACT

A smoke detecting microwave assembly for inhibiting fire when cooking with a microwave oven includes a microwave oven that has an interior space. A smoke detector is coupled to the microwave oven for detecting smoke. The smoke detector is electrically coupled to the microwave oven. The microwave oven is turned off when the smoke detector detects smoke to inhibit food from combusting in the microwave oven. A carbon monoxide detector is coupled to the microwave oven for detecting carbon monoxide. The microwave oven is turned off when the carbon monoxide detector detects carbon monoxide to inhibit production of carbon monoxide from combustion.

4 Claims, 4 Drawing Sheets

(56) References Cited

U.S. PATENT DOCUMENTS

| | | | | |
|---|---|---|---|---|
| 2011/0170377 A1* | 7/2011 | Legaspi | .................. | G08B 17/00 |
| | | | | 367/199 |
| 2014/0234496 A1* | 8/2014 | Siegel | ..................... | A47J 27/62 |
| | | | | 426/231 |
| 2017/0115010 A1* | 4/2017 | Martino | ................. | F24H 9/2085 |
| 2018/0220500 A1* | 8/2018 | Staton | ..................... | A47J 36/02 |

* cited by examiner

US 10,555,383 B1

SMOKE DETECTING MICROWAVE ASSEMBLY

CROSS-REFERENCE TO RELATED APPLICATIONS

Statement Regarding Federally Sponsored Research or Development

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to smoke detecting devices and more particularly pertains to a new smoke detecting device for inhibiting fire when cooking with a microwave oven.

BRIEF SUMMARY OF THE INVENTION

An embodiment of the disclosure meets the needs presented above by generally comprising a microwave oven that has an interior space. A smoke detector is coupled to the microwave oven for detecting smoke. The smoke detector is electrically coupled to the microwave oven. The microwave oven is turned off when the smoke detector detects smoke to inhibit food from combusting in the microwave oven. A carbon monoxide detector is coupled to the microwave oven for detecting carbon monoxide. The microwave oven is turned off when the carbon monoxide detector detects carbon monoxide to inhibit production of carbon monoxide from combustion.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
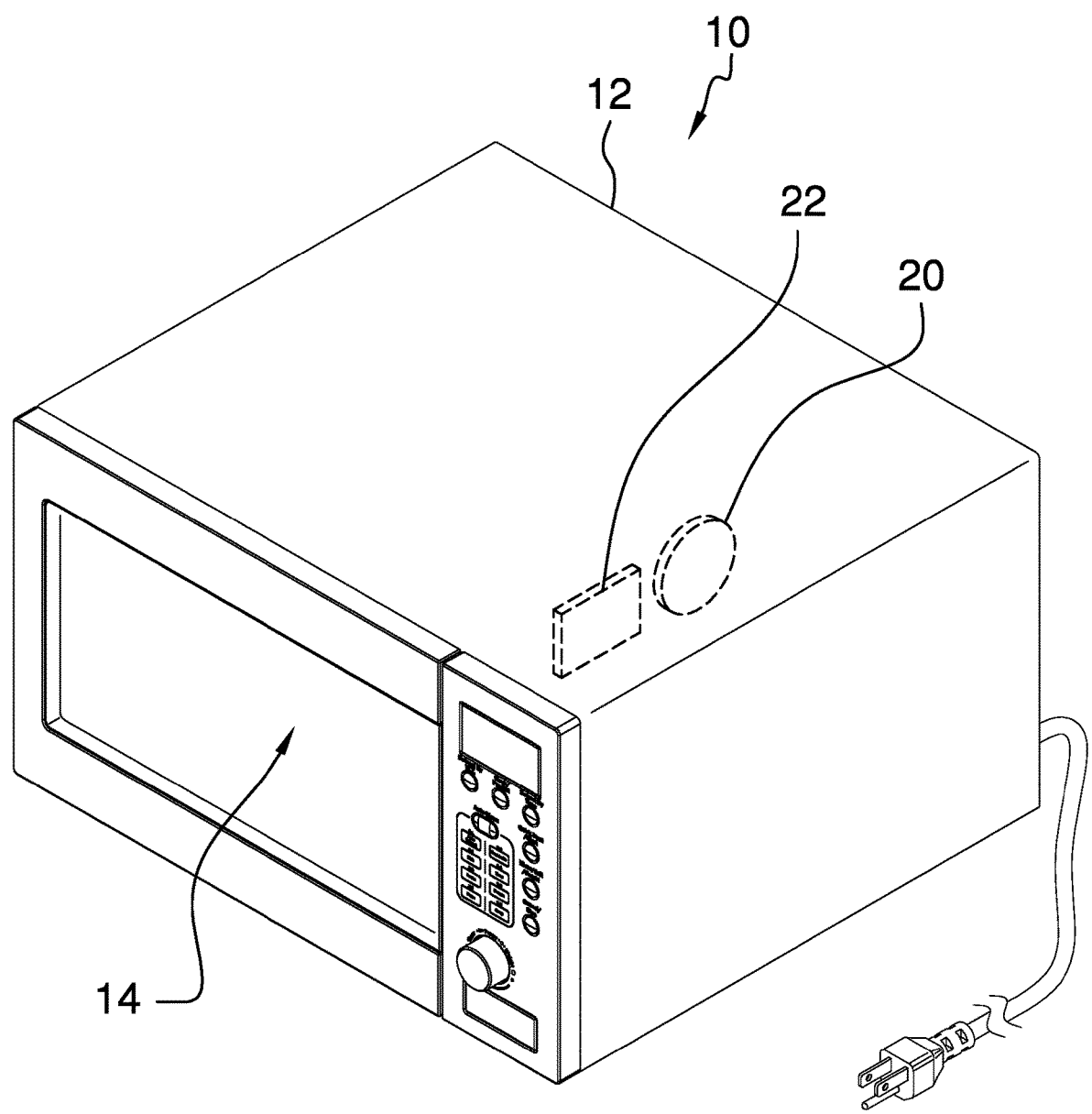
FIG. 1 is a perspective phantom view of a smoke detecting microwave assembly according to an embodiment of the disclosure.
Figure 2:
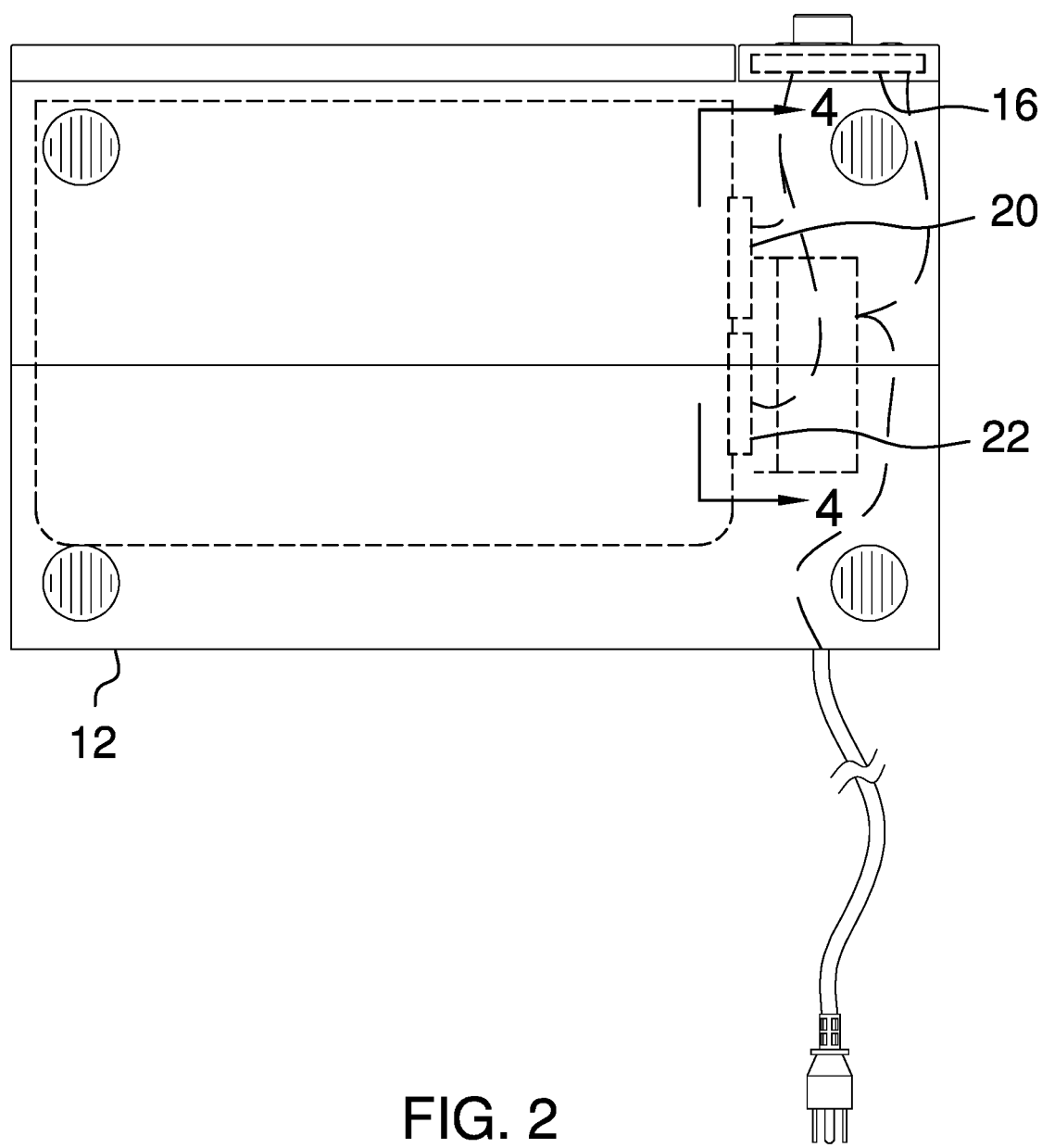
FIG. 2 is a bottom phantom view of an embodiment of the disclosure.
Figure 3:
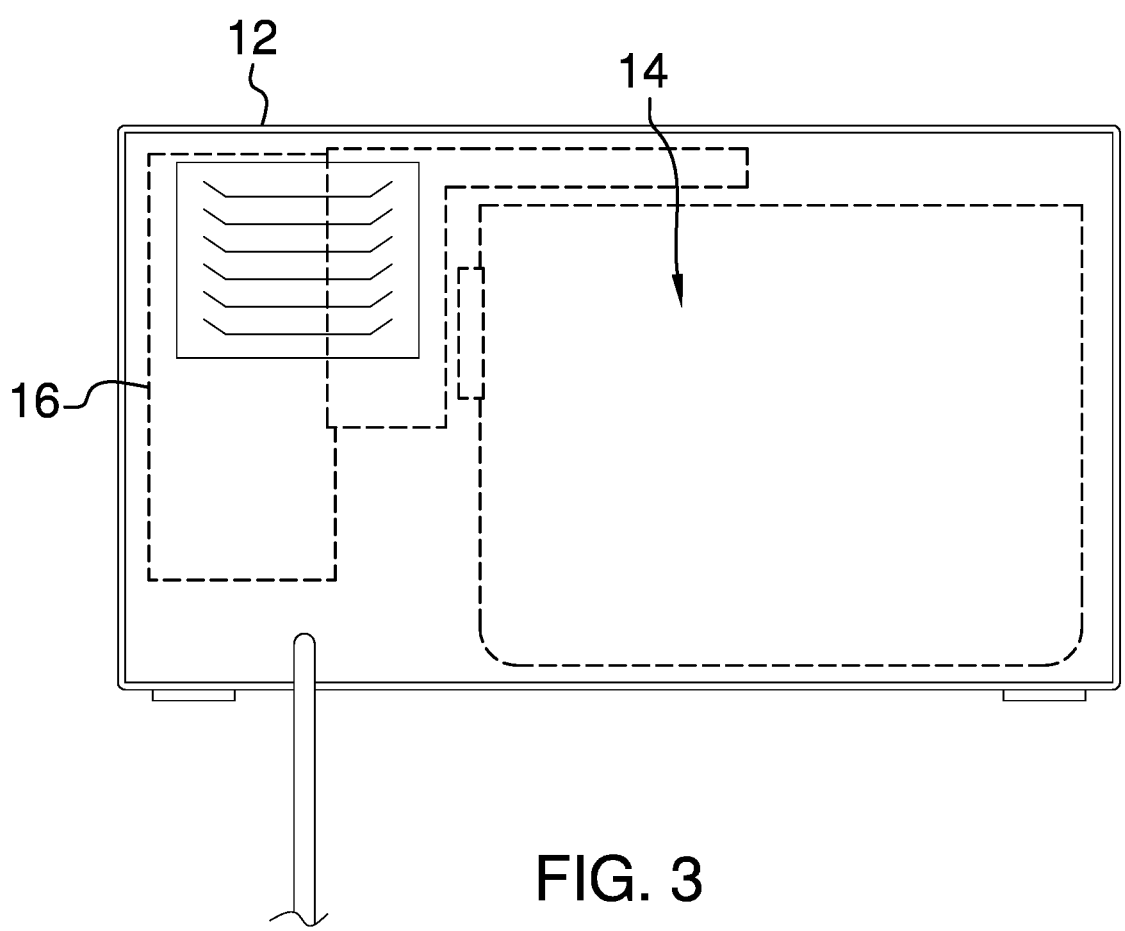
FIG. 3 is a back phantom view of an embodiment of the disclosure.
Figure 4:
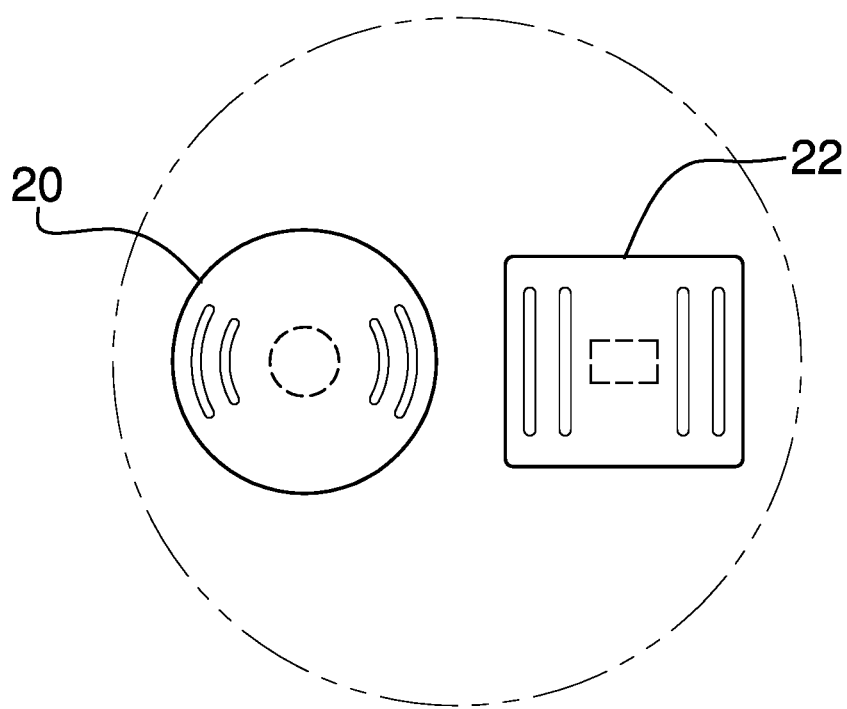
FIG. 4 is a front view of a smoke detector and a carbon monoxide detector of an embodiment of the disclosure.
Figure 5:
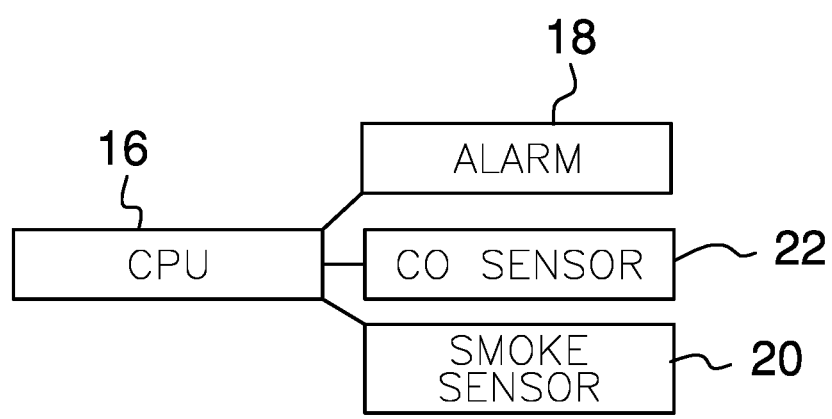
FIG. 5 is a schematic view of an embodiment of the disclosure.

With reference now to the drawings, and in particular to FIGS. 1 through 5 thereof, a new smoke detecting device embodying the principles and concepts of an embodiment of the disclosure and generally designated by the reference numeral 10 will be described.

As best illustrated in FIGS. 1 through 5, the smoke detecting microwave assembly 10 generally comprises a microwave oven 12 has an interior space 14. The microwave oven 12 may be an electronic microwave oven 12 of any conventional design. A control circuit 16 is positioned within the microwave oven 12 and the control circuit 16 comprises components common to microwave oven 12 control circuitry. Moreover, the control circuit 16 is in electrical communication with a remote alarm 18, such a electronic smoke detector or the like. The control circuit 16 may be hardwired to the remote alarm 18, the control circuit 16 may include a transmitter for wireless communication with the remote alarm 18, or the control circuit 16 may be in electrical communication with the remote alarm 18 through any conventional electronic means.

A smoke detector 20 is coupled to the microwave oven 12 the smoke detector 20 the electrically coupled to the control circuit 16. The smoke detector 20 is positioned in the interior space 14 such that the smoke detector 20 is in fluid communication with the interior space 14. The smoke detector 20 detects smoke and the control circuit 16 receives a smoke input when the smoke detector 20 detects smoke. Moreover, the control circuit 16 turns off the microwave oven 12 off when the control circuit 16 receives the smoke input. In this way the smoke detector 20 inhibits food from combusting in the microwave oven 12. Additionally, the remote alarm 18 the turned on when the control circuit 16 receives the smoke input. The remote alarm 18 emits an audible alarm to alert a user. The remote alarm 18 may be an existing smoke alarm in a house or the like.

A carbon monoxide detector 22 is provided and the carbon monoxide detector 22 is coupled to the microwave oven 12. The carbon monoxide detector 22 is positioned in the interior space 14 such that the carbon monoxide detector 22 is in fluid communication with the interior space 14. The carbon monoxide detector 22 detects carbon monoxide and the control circuit 16 receives a carbon monoxide input when the carbon monoxide detector 22 detects carbon monoxide. Moreover, the control circuit 16 turns off the microwave oven 12 when the control circuit 16 receives the carbon monoxide input. Thus, the carbon monoxide detector 22 inhibits the production of carbon monoxide from combustion. The remote alarm 18 is turned on when the control circuit 16 receives the carbon monoxide input to alert the user.

In use, the control circuit 16 receives the smoke input when the smoke detector 20 detects smoke in the microwave oven 12 from burning food. Thus, the microwave oven 12 is turned off thereby reducing the risk of fire resulting in the microwave. Additionally, the remote alarm 18 is turned on thereby alerting a user that food in the microwave oven 12 is burning. The control circuit 16 receives the carbon monoxide input when the carbon monoxide detector 22 detects carbon monoxide in the microwave oven 12. Thus, the microwave oven 12 is turned off and the alarm is turned on. In this way the smoke detector 20 and the carbon monoxide detector 22 enhance safety when the microwave oven 12 is used for cooking.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A smoke detecting microwave assembly for shutting off a microwave when food in the microwave begins to burn, said assembly comprising:
   a microwave oven having an interior space;
   a control circuit being positioned within said microwave oven, said control circuit being in electrical communication with a remote alarm, said control circuit being hardwired to said remote alarm, said remote alarm being an extrinsic smoke detector external to said microwave oven;
   an internal smoke detector being coupled to said microwave oven, said internal smoke detector detecting smoke, said internal smoke detector being electrically coupled to said microwave oven, said microwave oven being turned off when said internal smoke detector detects smoke wherein said internal smoke detector is configured to inhibit food from combusting in said microwave oven; and
   a carbon monoxide detector being coupled to said microwave oven, said carbon monoxide detector detecting carbon monoxide, said microwave oven being turned off when said carbon monoxide detector detects carbon monoxide wherein said carbon monoxide detector is configured to inhibit production of carbon monoxide from combustion.

2. The assembly according to claim 1, wherein:
   said internal smoke detector is electrically coupled to said control circuit, said internal smoke detector being positioned in said interior space such that said internal smoke detector is in fluid communication with said interior space, said control circuit receiving a smoke input when said internal smoke detector detects smoke, said control circuit turning off said microwave oven off when said control circuit receives said smoke input; and
   said remote alarm is turned on when said control circuit receives said smoke input having said remote alarm emitting an audible alarm wherein said remote alarm is configured to alert a user.

3. The assembly according to claim 1, wherein:
   said carbon monoxide detector is positioned in said interior space such that said carbon monoxide detector is in fluid communication with said interior space, said carbon monoxide detector being electrically coupled to said control circuit, said control circuit receiving a carbon monoxide input when said carbon monoxide detector detects carbon monoxide, said control circuit turning off said microwave oven when said control circuit receives said carbon monoxide input; and
   said remote alarm is turned on when said control circuit receives said carbon monoxide input having said remote alarm emitting an audible alarm wherein said remote alarm is configured to alert a user.

4. A smoke detecting microwave assembly for shutting off a microwave when food in the microwave begins to burn, said assembly comprising:
   a microwave oven having an interior space;
   a control circuit being positioned within said microwave oven, said control circuit being in electrical communication with a remote alarm said control circuit being hardwired to said remote alarm, said remote alarm being an extrinsic smoke detector external to said microwave oven;
   an internal smoke detector being coupled to said microwave oven, said internal smoke detector being electrically coupled to said control circuit, said internal smoke detector being positioned in said interior space such that said internal smoke detector is in fluid communication with said interior space, said internal smoke detector detecting smoke, said control circuit receiving a smoke input when said internal smoke detector detects smoke, said control circuit turning off said microwave oven off when said control circuit receives said smoke input wherein said internal smoke detector is configured to inhibit food from combusting in said microwave oven, said remote alarm being turned on when said control circuit receives said smoke input having said remote alarm emitting an audible alarm wherein said remote alarm is configured to alert a user; and
   a carbon monoxide detector being coupled to said microwave oven, said carbon monoxide detector being positioned in said interior space such that said carbon monoxide detector is in fluid communication with said interior space, said carbon monoxide detector detecting carbon monoxide, said control circuit receiving a carbon monoxide input when said carbon monoxide detector detects carbon monoxide, said control circuit turning off said microwave oven when said control circuit receives said carbon monoxide input wherein said carbon monoxide detector is configured to inhibit production of carbon monoxide from combustion, said remote alarm being turned on when said control circuit receives said carbon monoxide input having said remote alarm emitting an audible alarm wherein said remote alarm is configured to alert a user.

\* \* \* \* \*